United States Patent [19]

Goodhue et al.

[11] Patent Number: 4,588,683

[45] Date of Patent: May 13, 1986

[54] METHOD OF PREPARING 11β, 17α, 20, 21-TETRAHYDROXY STEROIDS AND CORRESPONDING 11β, 17α, 21-TRIHYDROXY-20-OXO STEROIDS

[75] Inventors: Charles T. Goodhue; Gwendolyn C. Kydd, both of Rochester, N.Y.; Charles H. Foster; Charles A. McCombs, both of Kingsport, Tenn.

[73] Assignee: Eastman Kodak Company, Rochester, N.Y.

[21] Appl. No.: 577,467

[22] Filed: Feb. 6, 1984

[51] Int. Cl.[4] .................... C12P 33/08; C12R 1/645
[52] U.S. Cl. .................................... 435/59; 435/911
[58] Field of Search ........................ 435/59, 60, 58

[56] References Cited

U.S. PATENT DOCUMENTS

| | | | |
|---|---|---|---|
| 2,658,023 | 11/1953 | Shull et al. | 435/59 |
| 3,264,194 | 8/1966 | Casas-Campillo | 435/59 |
| 3,419,470 | 12/1968 | Zaffaroni et al. | 435/59 |
| 3,530,038 | 9/1970 | de Flines et al. | 435/59 |
| 4,272,444 | 6/1981 | McCombs et al. | |
| 4,353,985 | 10/1982 | Petzoldt et al. | 435/59 |

FOREIGN PATENT DOCUMENTS 2803660 7/1979 Fed. Rep. of Germany .
2803661 7/1979 Fed. Rep. of Germany .
207496 2/1940 Switzerland .

OTHER PUBLICATIONS

Ruzicka, *Helv. Chim. Acta.*, 22, pp. 755–757 (1939).
Cremonesi et al., *Biotech. and Bioeng.*, 17, pp. 1101–1108 (1975).
Pfitzner et al., *J.A.C.S.*, 87, pp. 5661–5678 (1965).

*Primary Examiner*—Alvin E. Tanenholtz
*Attorney, Agent, or Firm*—J. Lanny Tucker

[57] ABSTRACT

Disclosed herein is a method for preparing 11β, 17α, 20, 21-tetrahydroxy steroids of the pregnane class. This method comprises incubating the corresponding 17α, 20α or β, 21-trihydroxy steroid in the presence of a culture medium capable of effecting the 11β-hydroxylation, such medium comprising a fungal culture of the genus Curvularia. Also disclosed herein is a method for preparing 11β, 17α, 21-trihydroxy-20-oxo steroids of the pregnane class. This method comprises the hydroxylation method described hereinabove followed by conversion of the resulting 11β, 17α, 20α or β, 21-tetrahydroxy steroid into the corresponding 11β, 17α, 21-trihydroxy-20-oxo steroid.

15 Claims, No Drawings

METHOD OF PREPARING 11β, 17α, 20, 21-TETRAHYDROXY STEROIDS AND CORRESPONDING 11β, 17α, 21-TRIHYDROXY-20-OXO STEROIDS

FIELD OF THE INVENTION

The present invention relates to a method of preparing 11β-hydroxy steroids. In particular, it relates to microbiological methods of preparing 11β, 17α, 20, 21-tetrahydroxy steroids and the corresponding 11β, 17α, 21-trihydroxy-20-oxo steroids.

BACKGROUND OF THE INVENTION

It is well known that 11β-hydroxy steroids exhibit anti-inflammatory activity. For example, hydrocortisone is an effective therapeutic agent for the treatment of rheumatoid arthritis and other inflammatory diseases. Such steroids, including cortisone, prednisolone, dexamethasone, betamethasone, prednylidene and flurandrenolone, can be produced from naturally occurring steroids by means of expensive, multistage synthesis.

An intensive research effort has been ongoing over many years to find methods for making 11β-hydroxy steroids using either chemical or microbiological techniques. The most difficult step in the synthesis of such compounds is the stereospecific introduction of the hydroxyl group at the C-11 position of the steroid molecule.

U.S. Pat. No. 2,658,023 (issued Nov. 3, 1953 to Shull et al) relates to a microbiological method of preparing hydrocortisone from a starting material represented by the formula:

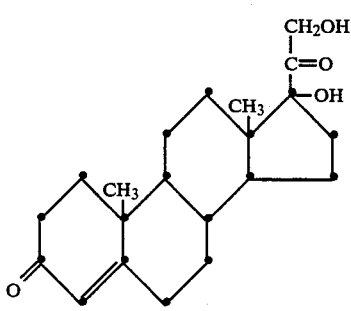

The method includes incubating the starting material in the presence of any of a number of microorganisms of the genus Curvularia, e.g. *Curvularia lunata*, and provides hydrocortisone in up to 40% yield. It would be desirable, however, to be able to make hydrocortisone at much higher yields.

U.S. Pat. No. 3,419,470 (issued Dec. 31, 1968 to Zaffaroni et al) relates to a similar method of making various steroids, including hydrocortisone, by hydroxylating the corresponding 11-desoxy compounds (some of which have bulky groups in the 17α-position) in the presence of *Curvularia lunata* and up to 50% (by volume) of dimethylsulfoxide in the reaction medium. This method is reported to provide a yield of hydrocortisone of up to about 78%. It is undesirable, however, to have dimethylsulfoxide or any other organic solvent in the reaction medium in large amounts in order to avoid destruction of the microorganism. U.S. Pat. No. 3,530,038 (issued Sept. 22, 1970 to de Flines et al) relates to the preparation of hydrocortisone by hydroxylating a 11-desoxy-20-oxo compound represented by the formula:

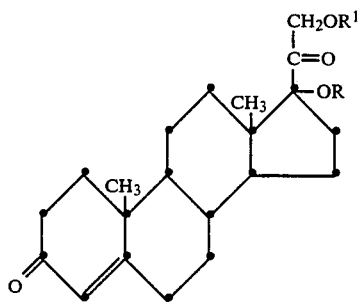

wherein R is an acyl of an organic carboxylic acid of 1 to 18 carbon atoms and $R_1$ is hydrogen or the same as R, in the presence of *Curvularia lunata*.

A more recent reference, U.S. Pat. No. 4,353,985 (issued Oct. 12, 1982 to Petzoldt et al.), relates to the preparation of hydrocortisone and related steroids by fermenting an 11-desoxy-20-oxo compound represented by the formula:

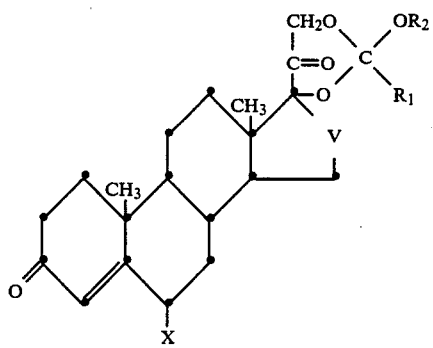

wherein represents a single bond or a double bond; X is hydrogen, fluorine, chlorine or methyl; V is methylene; ethylene, ethylidene or vinylidene; $R_1$ is hydrogen or $C_{1-6}$ alkyl; and $R_2$ is $C_{1-6}$ alkyl, in the presence of a fungal culture of the genus Curvularia (e.g. *Curvularia lunata*). High yields (85–90%) of hydrocortisone or related steroids are purportedly obtained with this method.

It appears that once the method of U.S. Pat. No. 2,658,023 was known, the object of many later researchers was to improve the yield of that method by hydroxylating 11-desoxy-20-oxo compounds having more bulky or complicated groups at the 17α and/or 21-positions. However, these starting materials are often difficult and very expensive to prepare. Yet, the known method which utilizes the simpler and less expensive starting material having a hydroxy group at the 17α and 21-positions, as in the '023 patent, provides undesirably low yields of desired steroids.

It would be desirable to have a method of preparing hydrocortisone and related steriods at high yields from relatively inexpensive and readily available starting materials.

SUMMARY OF THE INVENTION

We have found a novel method for preparing 11β-hydroxy steroids in high yields using relatively simple and inexpensive starting materials. The yields of desired steroids obtained with this invention are generally greater than 90%, which is a significant improvement over the less than 40% yield obtained from the method taught by U.S. Pat. No. 2,658,023. The starting materials for the method of this invention are readily obtained from soy sterols which are commercially available materials.

In accordance with this invention, an 11β, 17α, 20α or β, 21-tetrahydroxy steroid of the pregnane class is prepared by incubating the corresponding 17α, 20α or β, 21-trihydroxy steroid in the presence of a culture medium capable of effecting the 11β-hydroxylation. This medium comprises a fungal culture of the genus Curvularia or enzymes produced therefrom capable of effecting the hydroxylation.

This invention also provides a method for preparing the corresponding 11β, 17α, 21-trihydroxy-20-oxo steroids.

This process comprises the steps of:
a. hydroxylating a 17α, 20α or β, 21-trihydroxy steroid of the pregnane class in the 11β-position by incubating the trihydroxy steroid in the presence of a culture medium comprising a fungal culture of the genus Curvularia or enzymes produced therefrom to provide the corresponding 11β, 17α, 20α or β, 21-tetrahydroxy steroid; and
b. converting the tetrahydroxy steroid into the 11β, 17α, 21-trihydroxy-20-oxo steroid.

DETAILED DESCRIPTION OF THE INVENTION

The starting materials for the method of this invention are 17α, 20αor β, 21-trihydroxy steroids of the pregnane class. These steroids can be saturated or unsaturated as long as there are two hydrogen atoms at the 11-position. The higher or lower homologues, for example the corresponding A-nor-, D-homo- or 19-nor- compounds, can also be used in the practice of this invention. Double bonds can be present, for example, in the 1-, 2-, 3-, 4-, 5-, 6-, 7-, 8-, 8(14), 14- or 15-positions and a fused ring can be present bridging the 2- and 3-positions.

As indicated hereinabove, the starting materials have hydroxy groups in the 17α, 20α or β- and 21-positions. In a preferred embodiment, the hydroxy group in the 20-position is β. These compounds can be further substituted, if desired, in any position where a hydrogen atom can be removed, except at the 11-position. Examples of possible substituents at other positions include hydroxy and corresponding esters having up to 18 carbon atoms; oxo; aryloxy having up to 14 carbon atoms in the aromatic nucleus (e.g. phenoxy, etc.); substituted or unsubstituted alkyl of 1 to 18 carbon atoms including alkylaryl (e.g. methyl, ethyl, isopropyl, t-butyl, chloromethyl, benzyl, etc.); substituted or unsubstituted alkoxy of 1 to 18 carbon atoms (e.g. methoxy, n-propoxy, t-butoxy, etc.); substituted or unsubstituted aryloxy of 6 to 14 carbon atoms in the aromatic nucleus (e.g. phenoxy); halo (e.g. fluoro, chloro, bromo, etc.); substituted or unsubstituted aryl of 6 to 14 carbon atoms in the aromatic nucleus (e.g. phenyl, xylyl, p-chlorophenyl), etc.); and heteroatoms (e.g. substituted or unsubstituted thiols, amines or phosphorus moieties).

Steroid compounds which are particularly useful in the practice of this invention are represented by the formula:

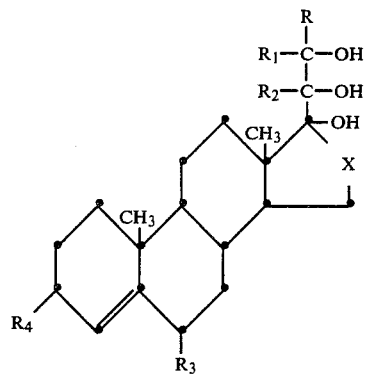

wherein represents a single bond or a double bond. R, $R_1$ and $R_2$ are independently hydrogen or substituted or unsubstituted alkyl of 1 to 18 carbon atoms including alkylaryl (e.g. methyl, ethyl, isopropyl, t-butyl, benzyl, chloromethyl, etc.); $R_3$ is hydrogen, alkyl as defined for R, $R_1$ and $R_2$, or halo (e.g. fluoro, chloro, bromo, etc.); X is substituted or unsubstituted methylene, ethylene, ethylidene or vinylidene; and $R_4$ is hydroxy or oxo.

Preferably, is a single bond, X is methylene; each of R, $R_1$ and $R_2$ is hydrogen; and $R_4$ is oxo. More preferably, $R_3$ is also hydrogen.

Examples of useful starting materials include, but are not limited to: 17α, 20β, 21-trihydroxy-4-pregnen-3-one; 17α, 20β, 21-trihydroxy-1,4-pregnadien-3-one; 17α, 20β, 21-trihydroxy-6-methyl-4-pregnen-3-one; 17α, 20β, 21-trihydroxy-6-chloro-4,6-pregnadien-3-one; 17α, 20β, 21-trihydroxy-6-ethyl-1,4,6-pregnatrien-3-one; pregnatrien-3-one; 17α, 20β, 21-trihydroxy-16-methyl-4-pregnen-3-one; 17α, 20β, 21-trihydroxy-16-methylene-1,4-pregnadien-3-one; 17α, 20β, 21-trihydroxy-D-homo-4-pregnen-3-one; 17α, 20β, 21-trihydroxy-20-methyl-4-pregnen-3-one; 21-dimethyl-17α, 20β, 21-trihydroxy-4-pregnen-3-one; 17α, 20α, 21-trihydroxy-4-pregnen-3-one; and 17α, 20β, 21-trihydroxy-21-chloromethyl-4-pregnen-3-one. A preferred compound in the practice of this invention is 17α, 20β, 21-trihydroxy-4-pregnen-3-one.

The trihydroxy steroids useful in the practice of this invention are readily prepared from commercially available soy sterols using procedures known in the art. For example, a preferred starting material, 17α, 20β, 21-trihydroxy-4-pregnen-3-one, can be prepared by reaction of 17α-hydroxy-4,20-pregnadien-3-one with osmium tetroxide [see Ruzicka Helv. Chim. Acta, 22, pp. 755–757 (1939)]; by reduction of a 3-enol ester of a 17,21-diacetoxy-4-pregnene-3,20-dione followed by saponification [see Swiss Pat. No. 207,496 (issued Feb. 16, 1940)] or by following the teaching of U.S. Pat. No. 4,272,444 (issued June 9, 1981 to McCombs et al).

The above-identified trihydroxy steroids are used in the practice of this invention to prepare the corresponding 11β, 17α, 20α or β, 21-tetrahydroxy steroids by hydroxylation of the trihydroxy steroids in the 11β-position. This hydroxylation is accomplished by incubating the starting materials in the presence of a culture medium capable of effecting the 11β-hydroxylation. This method comprises the use of a fungus of the genus Curvularia or enzymes produced therefrom. The enzymes can be used alone, if desired, when isolated from the microorganism; or a suspension of spores, or whole or lysed cells can be used. Preferably, the microorganisms themselves are used in the practice of this invention to avoid additional manufacturing steps. This incubation is carried out under conditions customarily employed for 11β-hydroxylation with Curvularia microorganisms. Generally, incubation is carried out at a temperature of up to 40° C., and preferably in the range of from about 20° to about 30° C., for up to 48 hours, and preferably from about 6 to about 24 hours. The microorganisms or enzymes therefrom can be immobilized on a suitable substrate if desired.

Oxygenating species of fungi of the genus Curvularia suitable for the 11β-hydroxylation include, for example, *Curvularia falcata, Curvularia genticulata, Curvularia brachyspora, Curvularia pallescens, Curvularia lunata* and *Curvalaria maculans*. The species *Curvularia lunata* is preferred. Many of these microorganisms are available in public culture collections and others can be isolated from natural materials, such as soil, by standard procedures known to mycologists.

In a suitable culture medium, submerged cultures are grown under aeration using culturing conditions (e.g. carbon and nitrogen sources, concentration, growth promotors, pH, temperature, etc.) customarily employed for these microorganisms as described, for example, by Charnay and Herzog, *Microbiological Transformation of Steroids*, 1967, Academic Press, New York. The trihydroxy steroid starting material can be added to the culture as a powder, in an emulsified form or dissolved in a suitable organic solvent. The concentration of the starting material (also known as a substrate) in the culture medium can be up to 5, and preferably in the range of from about 0.1 to about 1, percent, based on total weight of the culture medium.

Suitable solvents for dissolving the substrate include, for example, methanol, ethanol, propylene glycol, acetone, glycol monomethyl ether, dimethylformamide and dimethyl sulfoxide. Care must be taken, however, to keep the level of any such solvent used below that which adversely affects the microorganisms, i.e. generally less than about 1 percent, by volume. The steroid substrate can be emulsified, for example, by introducing it via nozzles in micronized form or dissolved in a water-miscible solvent under high turbulence into a suitable water-containing emulsifier. Suitable emulsifiers include, for example, nonionic surfactants, e.g. ethylene oxide adducts or fatty acid esters of polyglycols. Suitable water-miscible solvents include, for example, the substrate solvents noted hereinabove in this paragraph.

The specific details of incubation to provide a particular tetrahydroxy steroid are provided in Example 1 hereinbelow. The optimum substrate concentration, time of substrate addition and duration of fermentation are dependent upon the structure of the trihydroxy steroid and upon the species of microorganism used in the hydroxylation. These variables can be readily determined in each individual hydroxylation reaction with routine preliminary experimentation within the expertise of one of ordinary skill in the art.

The yield of 11β, 17α, 20α or β, 21-tetrahydroxy steroid obtained from the method of this invention will vary depending upon the incubation conditions employed, but generally the yield is greater than about 90% of the theoretical yield based on amount of starting material. A worker skilled in the art can, with routine experimentation, select the optimum conditions, including the best microorganism for a given starting material, to provide optimum yield.

The method of this invention is preferably used to obtain tetrahydroxy steroids of the formula:

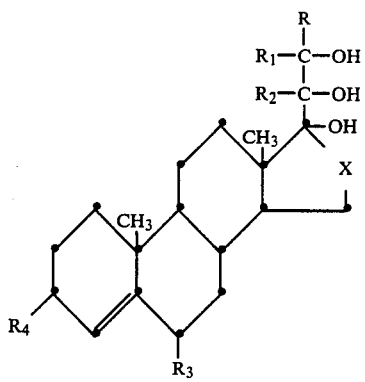

wherein , X, R, $R_1$, $R_2$, $R_3$ and $R_4$ are as described hereinabove.

The 11β, 17α, 20α or β, 21-tetrahydroxy steroids prepared according to this invention can be used as intermediates in a method for preparing corresponding 11β, 17α, 21-trihydroxy-20-oxo steroids of the pregnane class. In this method, the tetrahydroxy steroid is converted to the corresponding trihydroxy-20-oxo steroid using techniques known in the art. Generally, these techniques comprise converting the 20α or β-hydroxy group into a 20-oxo group. For example, the preferred tetrahydroxy steroid noted hereinabove can be converted to hydrocortisone (11β, 17α, 21-trihydroxy-4-pregnene-3,20-dione) by the procedure described by Cremonesi et al, *Biotech. and Bioeng.*, 17, pp. 1101–1108 (1975). This procedure uses the enzyme 20β-hydroxysteroid: NAD+ oxidoreductase (E.C. 1.1.1.53) in a two-phase environment to oxidize the 20β-hydroxy group to the 20-oxo group, or to reduce the 20-oxo group to the 20β-hydroxy group. Under mildly basic conditions, the oxidation reaction can be made to predominate.

An alternative conversion method comprises converting the C-21 hydroxy group in the tetrahydroxy steroid to an acetate or a phosphate, oxidizing the 20-hydroxy group to the oxo group using the Pfitzner-Moffatt oxidation [Pfitzner et al, *J.A.C.S.*, 87, 5661 (1965); and 87, 5670 (1965)], and converting the acetate or phosphate at the C-21 position back to a hydroxy group.

The examples which follow are intended to illustrate, but not limit, the practice of this invention. In these examples, the *Curvularia lunata* microorganism was obtained from the American Type Culture Collection (ATCC #12017) located in Rockville, Md.; yeast malt extract agar and Saboraud dextrose agar were purchased from Difco Labs, Inc., Detroit, Mich. and Baltimore Biological Labs, Cockeysville, Md., respectively; and corn steep liquor was obtained from Corn Products International, Argo, Ill.

EXAMPLE 1

Preparation of 11β, 17α, 20β, 21-Tetrahydroxy-4-pregnen-3-one

*Curvularia lunata* microorganisms were transferred from slants of yeast malt extract agar or Saboraud dextrose agar and grown in 250 mL flasks using 25 mL of a first culture medium containing 20 g/L of corn steep liquor and 20 g/L of glucose. The pH of the culture medium was adjusted to 6.2 using concentrated potassium hydroxide. The culture medium was then incubated on a Model G-26 Psycrotherm TM shaker (available from New Brunswick Scientific Co. located in New Brunswick, New Jersey) operating at 200 rpm and 26° C.

After 3 days under such conditions, an 8–10% (volume per volume) inoculum of the first culture medium was used to seed 250 mL flasks containing 50 mL of a second culture medium containing 5 g/L of corn steep liquor and 5 g/L of glucose. The pH of this medium was similarly adjusted to 6.2 and the flasks were incubated as described hereinabove for 30 hours.

A 10% inoculum of the second culture medium was added to a 250 mL flask containing 50 mL of a third culture medium containing 40 g/L of corn steep liquor and 8 g/L of glucose. The pH of this medium was similarly adjusted to 6.2 and incubated as described hereinabove for 10 hours.

Then, 17α, 20β, 21-trihydroxy-4-pregnen-3-one was added as a 1% solution in dimethylformamide to the third culture medium such that the final concentration of the steroid was 0.05% (by weight). The resulting solution was incubated at 26° C. and 200 rpm for 24 hours as described hereinabove to promote hydroxylation of the trihydroxy steroid.

The entire contents of several of the flasks were extracted with a volume of dichloromethane equal to one half the volume of the flask after 15 hours into the incubation and after 24 hours into the incubation and mixed by shaking on a conventional rotary shaker over 30 minutes. The organic layer was allowed to settle for 30 minutes, separated and the process repeated. The combined extracts were then analyzed by high performance liquid chromatography to determine the amount of tetrahydroxy steroid product present. The chomatography was performed using a Varian Model 5021 liquid chromatograph equipped with an automatic loop injector (Rheodyne Model 7125) and a Varian Varichrome TM UV-50 variable wavelength detector. Peak areas and retention times were determined with a Varian CDS-111L laboratory data system. Steroids and transformation products were separated using a $C_{18}$ reversed-phase Micro-Pak TM MCH-10 column (30 cm×4 mm I.D.) and a solvent system of acetonitrile/water (10:40, by volume). Operating conditions were a flow rate of 2 mL/min., UV detection at 254 nm, chart speed at 1 cm/min. and elutions run at ambient temperature. The chromatography curves were characterized against control curves of known compounds.

The results of the liquid chromotography analysis are presented in Table I below. They indicate a conversion of the 17α, 20β, 21-trihydroxy starting material into the corresponding 11β, 17α, 20β, 21-tetrahydroxy steroid at high yields, particularly after the 24 hour incubation time. The present yield of each compound was determined by dividing the peak area of each compound by the total area of all products in the medium, and multiplying the dividend by 100.

TABLE I

| | Compound Yield (%) | | |
|---|---|---|---|
| Incubation Time (hours) | Tetrahydroxy Steroid | Trihydroxy Steroid | Side Products |
| 15 | 77 | 16 | ND* |
| 24 | 92 | ND* | ND* |

*ND = none detected

EXAMPLE 2

This is a comparative example comparing the yield of 11β-hydroxylated steroid prepared by the method of this invention to the yield obtained with a method similar to that taught in U.S. Pat. No. 3,419,470 (noted hereinabove) except that dimethylformamide was used in place of dimethylsulfoxide.

Both 17α, 20β, 21-trihydroxy-4-pregnen-3-one and 17α-acetoxy-4-pregnene-3,20-dione (one of the starting materials taught by the '470 patent) were subjected to the following tests and analyzed for conversion to the corresponding 11β-hydroxylated steroid product.

Test A: Steroid Added to Culture Medium as Fine Powder

This test was conducted in a 250 mL flask containing 50 mL of a culture medium composed of 40 g/L corn steep liquor and 8 g/L of glucose at a pH of 6.2. *Curvularia lunata* microorganisms (100 mg, dry) and steroid starting material (25 mg) were added. The resulting mixture was incubated for 32 hours and extracted with dichloromethane as described in Example 1. The extracts were analyzed by thin-layer chromatography using Whatman LHP-Rf plates, developed with acetone/dichloromethane (1:4 by volume), and quantitative densitometric measurements of the eluted spots were determined at 254 nm with a conventional spectrodensitometer.

Test B: Steroid Added to Culture Medium in Dimethylformamide

The culture medium for this test was prepared like that of Test A except that the culture medium was incubated 2 hours prior to addition of the steroid substrate and the steroid starting material was added in dimethylformamide such that the resulting steroid concentration was 0.05% (weight per volume) in the culture medium and the solvent concentration did not exceed 1% (v/v). Following addition of the starting material, the resulting mixture was incubated for 24 hours and extracted with dichloromethane as described in Example 1. The extracts were analyzed by high performance liquid chromatography as described in Example 1.

The results of conversion to 11β-hydroxylated steroids from these Tests are presented in Table II below. It is apparent from these results that use of the dimethylformamide (which is a solvent similar to dimethylsulfoxide) in Test B significantly improves the conversion yield of 17α-acetoxy-4-pregnene-3,20-dione but has little affect on the conversion yield of the 17α, 20β, 21-trihydroxy steroid which is useful in the practice of this invention. Thus, in the practice of this invention, there is desirable latitude as to how the steroid starting materials can be added to the culture medium in order to obtain high yields.

TABLE II

| Steroid Starting Material | 11β-Hydroxylation Conversion Yield (%) | |
|---|---|---|
| | Test A | Test B |
| 17α, 20β, 21-trihydroxy-4-pregnen-3-one | 89 | 92 |
| 17α-acetoxy-4-pregnene-3,20-dione | 15 | 72 |

The 11β, 17α, 20β, 21-tetrahydroxy-4-pregnen-3-one steroid prepared in this example can be converted to 11β, 17α, 21-trihydroxy-4-pregnene-3,20-dione by the following procedure which is described in more detail by Cremonesi et al in *Biotech. and Bioeng.*, 17, pp. 1101–1108 (1975). The tetrahydroxy steroid (0.01–0.2 M) can be oxidized at the C-20 position in a mildly basic environment (e.g. pH 8–9) in the presence of the enzyme 20β-hydroxy steroid: NAD+ oxidoreductase. Other reagents present in this reaction include NAD+ (nicotinamide adenine dinucleotide) (0.01–0.2 M); a suitable buffer, e.g. tris(hydroxymethyl)aminomethane (0.05–0.2 M) and optionally, a ketone trapping agent, e.g. hydroxylamine (0.01–0.2 M). Butyl acetate can be used to dissolve the steroid.

The invention has been described in detail with particular reference to preferred embodiments thereof, but it will be understood that variations and modifications can be effected within the spirit and scope of the invention.

We claim:

1. A method for preparing an 11β, 17α, 20α or β, 21-tetrahydroxy steroid, said method comprising incubating a 17α, 20α or β, 21-trihydroxy steroid of the pregnane class in the presence of a culture medium capable of effecting 11β-hydroxylation of said trihydroxy steroid, said medium comprising a fungal culture of the genus Curvularia or enzymes produced therefrom.

2. The method of claim 1 wherein said culture medium comprises a fungal culture of the species *Curvularia lunata* or enzymes produced therefrom.

3. The method of claim 1 wherein the 11β, 17α, 20β, 21-tetrahydroxy steroid is prepared.

4. The method of claim 1 wherein said trihydroxy steroid is represented by the formula:

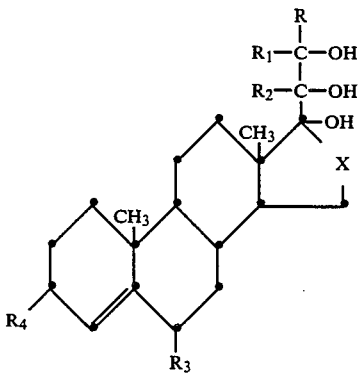

wherein represents a single bond or a double bond; X is methylene, ethylene, ethylidene or vinylidene; R, R₁ and R₂ are independently hydrogen or alkyl of 1 to 18 carbon atoms; R₃ is hydrogen, alkyl of 1 to 18 carbon atoms or halo; and R₄ is hydroxy or oxo.

5. The method of claim 4 wherein R₄ is oxo.

6. The method of claim 5 wherein represents a single bond; X is methylene; and each of R, R₁, and R₂ is hydrogen.

7. The method of claim 6 wherein R₃ is hydrogen.

8. A method for preparing 11β, 17α, 20β, 21-tetrahydroxy-4-pregnen-3-one, said method comprising incubating 17α, 20β, 21-trihydroxy-4-pregnen-3-one in the presence of a culture medium capable of effecting 11β-hydroxylation of said trihydroxy steroid, said medium comprising a fungal culture of the species *Curvularia lunata* or enzymes produced therefrom.

9. A method for preparing an 11β, 17α, 21-trihydroxy-20-oxo steroid, said method comprising the steps of:

a. hydroxylating a 17α, 20α or β, 21-trihydroxy steroid of the pregnane class in the 11β-position by incubating said trihydroxy steroid in the presence of a culture medium comprising a fungal culture of the genus Curvularia or enzymes produced therefrom to provide the corresponding 11β, 17α, 20α or β, 21-tetrahydroxy steroid; and b. converting said tetrahydroxy steroid into said 11β, 17α, 21-trihydroxy-20oxo steroid.

10. The method of claim 9 wherein the 11β, 17α, 20β, 21-tetrahydroxy steroid is prepared in step a.

11. The method of claim 9 wherein said trihydroxy steroid is represented by the formula:

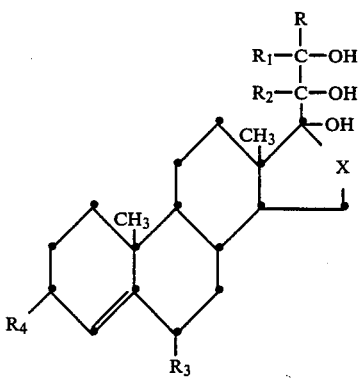

wherein represents a single bond or a double bond; X is methylene, ethylene, ethylidene or vinylidene; R, R₁ and R₂ are independently hydrogen or alkyl of 1 to 18 carbon atoms; R₃ is hydrogen, alkyl of 1 to 18 carbon atoms or halo; and R₄ is hydroxy or oxo.

12. The method of claim 11 wherein represents a single bond; X is methylene; each of R, R₁ and R₂ is hydrogen; and R₄ is oxo.

13. The method of claim 12 wherein R₃ is hydrogen.

14. The method of claim 9 wherein said culture medium comprises a fungal culture of the species *Curvularia lunata* or enzymes produced therefrom.

15. A method for preparing hydrocortisone, said method comprising the steps of:

a. hydroxylating 17α, 20β, 21-trihydroxy-4-pregnen-3-one in the 11β-position by incubating said trihydroxy steroid in the presence of a culture medium comprising a fungal culture of the species *Curvularia lunata* or enzymes produced therefrom capable of effecting said hydroxylation to provide 11β, 17α, 20β, 21-tetrahydroxy-4-pregnen-3-one; and b. converting said tetrahydroxy steroid into hydrocortisone.

* * * * *

UNITED STATES PATENT AND TRADEMARK OFFICE
CERTIFICATE OF CORRECTION

PATENT NO. : 4,588,683         Page 1 of 2
DATED      : May 13, 1986
INVENTOR(S): C. T. Goodhue; G. C. Kydd; C. H. Foster; C. A. McCombs It is certified that error appears in the above-identified patent and that said Letters Patent are hereby corrected as shown below:

Col. 2, lines 25-39;
Col. 4, lines 1-15;
Col. 6, lines 5-15;
Col. 9, lines 38-53; and
Col. 10, lines 25-39, the formula should read:

"  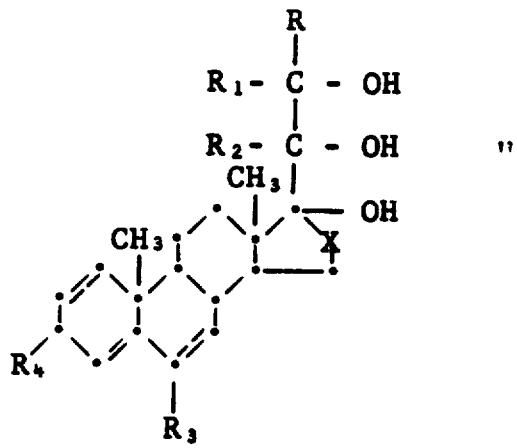  "

UNITED STATES PATENT AND TRADEMARK OFFICE
CERTIFICATE OF CORRECTION

PATENT NO. : 4,588,683

DATED : May 13, 1986

INVENTOR(S) : C. T. Goodhue; G. C. Kydd; C. H. Foster; C. A. McCombs

It is certified that error appears in the above-identified patent and that said Letters Patent are hereby corrected as shown below:

Col. 2, line 41, delete "wherein " and substitute therefor -- wherein - - --.

Col. 4, line 18, delete "wherein " and substitute therefor -- wherein - - --; line 26, delete "Preferably, " and substitute therefor --Preferably, - - --.

Col. 6, line 19, delete "wherein " and substitute therefor -- wherein - - --.

Col. 9, lines 54 and 61, delete "wherein " and substitute therefor -- wherein - - --.

Col. 10, line 15, delete "Curvularia" and substitute therefor --*Curvularia*--; lines 41 and 46, delete "wherein " and substitute therefor -- wherein - - --.

Signed and Sealed this

Ninth Day of December, 1986

Attest:

DONALD J. QUIGG

Attesting Officer     Commissioner of Patents and Trademarks